US00PP12085P2

(12) United States Plant Patent
Littlejohn et al.

(10) Patent No.: US PP12,085 P2
(45) Date of Patent: Sep. 11, 2001

(54) *ORNITHOGALUM DUBIUM* PLANT NAMED 'NAMIB SUNRISE'

(76) Inventors: Gail Littlejohn, Private Bag X1, Elsenberg 7607; E. L. Farringer; C. F. Farringer, both of P.O. Box 145, Groot Drakenstein, 7680, all of (ZA)

( * ) Notice: Subject to any disclaimer, the term of this patent is extended or adjusted under 35 U.S.C. 154(b) by 0 days.

(21) Appl. No.: 09/337,804

(22) Filed: Jun. 21, 1999

(51) Int. Cl.[7] ..... A01H 5/00

(52) U.S. Cl. ..... Plt./263

(58) Field of Search ..... Plt./263

(56) References Cited

PUBLICATIONS

UPOV ROM GTITM Computer Database 2000/04, GTI JOUVE Retrival Software, citation for 'NAMIB SUNRISE', Aug. 2000.*

* cited by examiner

*Primary Examiner*—Bruce R. Campell
*Assistant Examiner*—W. C. Baker
(74) *Attorney, Agent, or Firm*—Paul S. Rooy

(57) ABSTRACT

'Namib Sunrise', an *Ornithogalum dubium* cultivar. 'Namib Sunrise' has a compact growth habit with three to eight leaves which grow to a length of up to eight–twelve cm. The most striking characteristic of the mature plant is its corymbose-shaped inflorescence (raceme) which is between 15 and 30 cm tall and includes 15–20 flowers. The flowers are RHS25A orange with no darkened centers. Each 'Namib Sunrise' flower is cup-shaped, and 2.8 to 3 cm wide.

2 Drawing Sheets

FIELD OF THE INVENTION

The present invention comprises a new and distinct cultivar of *Ornithogalum dubium* which is named 'Namib Sunrise'. Its market class is that of potted plants or bulbs. 'Namib Sunrise' is intended for use in landscaping, and as a decorative flowering potted plant.

DESCRIPTION OF PRIOR ART

'Namib Sunrise' was invented by the selection of a single plant that originated from the progeny of the parent plants that were allowed to open-pollinate within the group. The pollination occurred during 1991 at Elsenberg, Western Cape, Republic of South Africa. 'Namib Sunrise' was bred and evaluated by Dr. Gail Littlejohn, a citizen of South Africa. 'Namib Sunrise' was first asexually propagated by Dr. E. L. Farringer and Mrs. C. F. Farringer. Dr. E. L. Farringer is a U.S. citizen, and Mrs. C. F. Farringer is a citizen of the Republic of South Africa.

'Namib Sunrise' is a selection of open-pollinated *Ornithogalum dubium*. The open pollination was achieved in a greenhouse, and was amongst a select population of *Ornithogalum dubium* individuals.

'Namib Sunrise' has been asexually reproduced in South Africa from 1997 onwards, using tissue culture. Approximately 20,000 plants have been grown, and these 'Namib Sunrise' propagules appear to be identical to the original plant in all distinguishing characteristics. Thus the clone appears stable.

'Namib Sunrise' is a bulbous plant with strap-like leaves of about 8 to 12 cm in length. In nature, it grows in winter and flowers in the spring (October in the Southern hemisphere at 32 degrees South). It produces a raceme somewhat corymbose in shape and lengthening with age to about 15–30 cm in height. Flowers are 2.8–3.5 cm in diameter and cup-shaped, with 15–20 flowers per inflorescence.

'Namib Sunrise' is cyclically dormant. Specifically, it is dormant in summer, and blooms every year. Plants in nature rarely live beyond 5–10 years due to pests. In a pest-free environment, plants will live in excess of 10 years. 'Namib Sunrise' is adapted to Zone 8 of the Hardiness Map of the United States.

'Namib Sunrise' is distinguishable from other clones by the color of its flower, the size and shape of the flower raceme, and the size of individual flowers as well as the compact growth pattern of the leaves.

'Namib Sunrise' is distinguished from other *Ornithogalum dubium* cultivars by the following combination of traits:

Flower color: RHS25A orange clear throughout the flower, with no dark center or heart.
Flower size: 2.8–3.5 cm.
Flower shape: Cup-shaped.
Raceme size: 15–30 cm in height.
Raceme shape: Corymbose, lengthening with age.
Flowers per raceme: 15–20 [50–60].
Leaf size: 8–12 cm.

BRIEF DESCRIPTION OF THE DRAWINGS

The inventon, together with the other objects, features, aspects and advantages thereof will be more clearly understood from the following in conjunction with the accompanying drawings.

Two sheets of drawings are provided. Sheet one contains FIG. 1. Sheet two contains FIG. 2.

BOTANICAL DESCRIPTION OF THE PLANT

Figure 1:
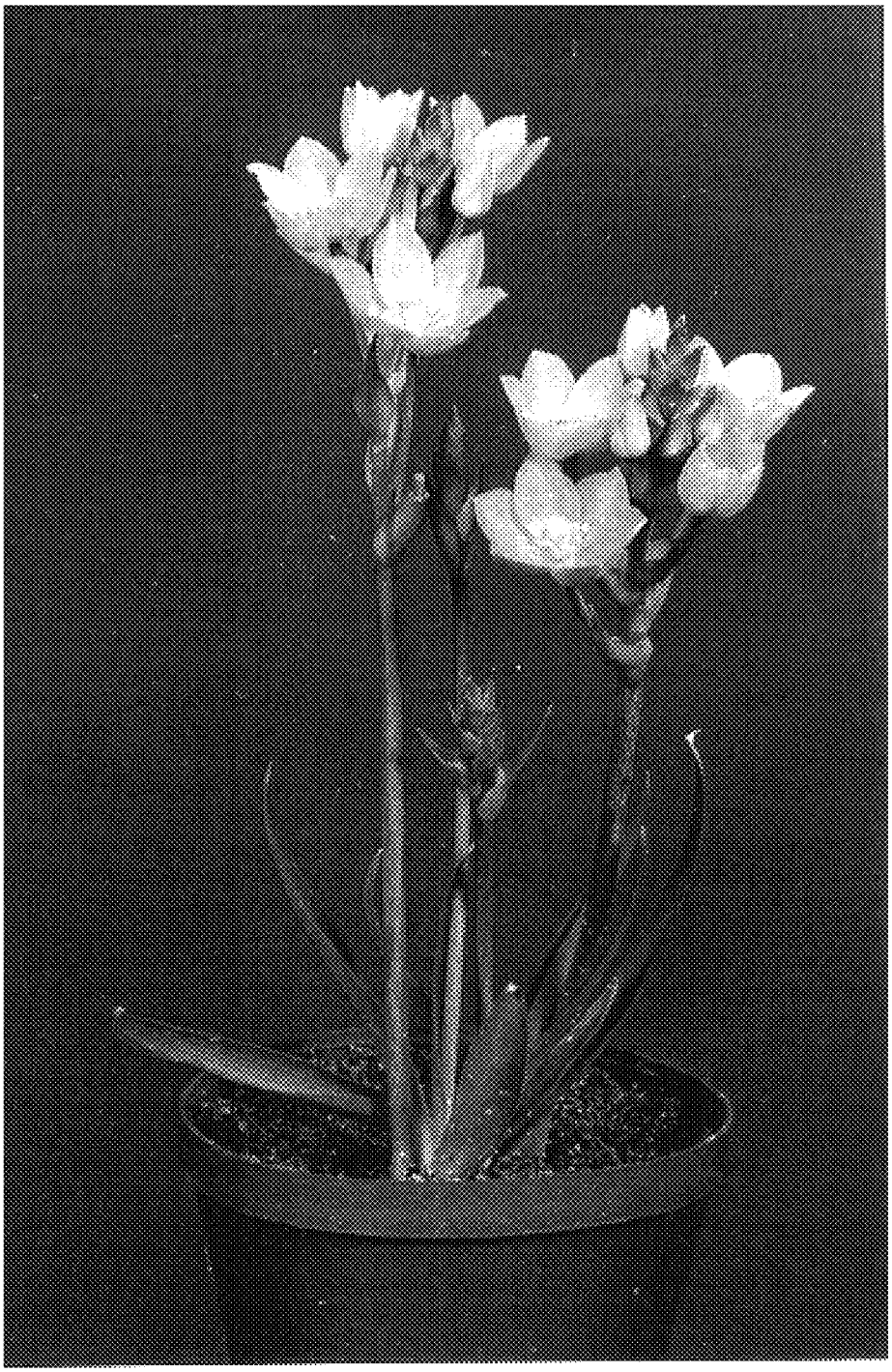
FIG. 1 is a color photograph of a 'Namib Sunrise' plant from its pot to its top, including the leaves.
Figure 2:
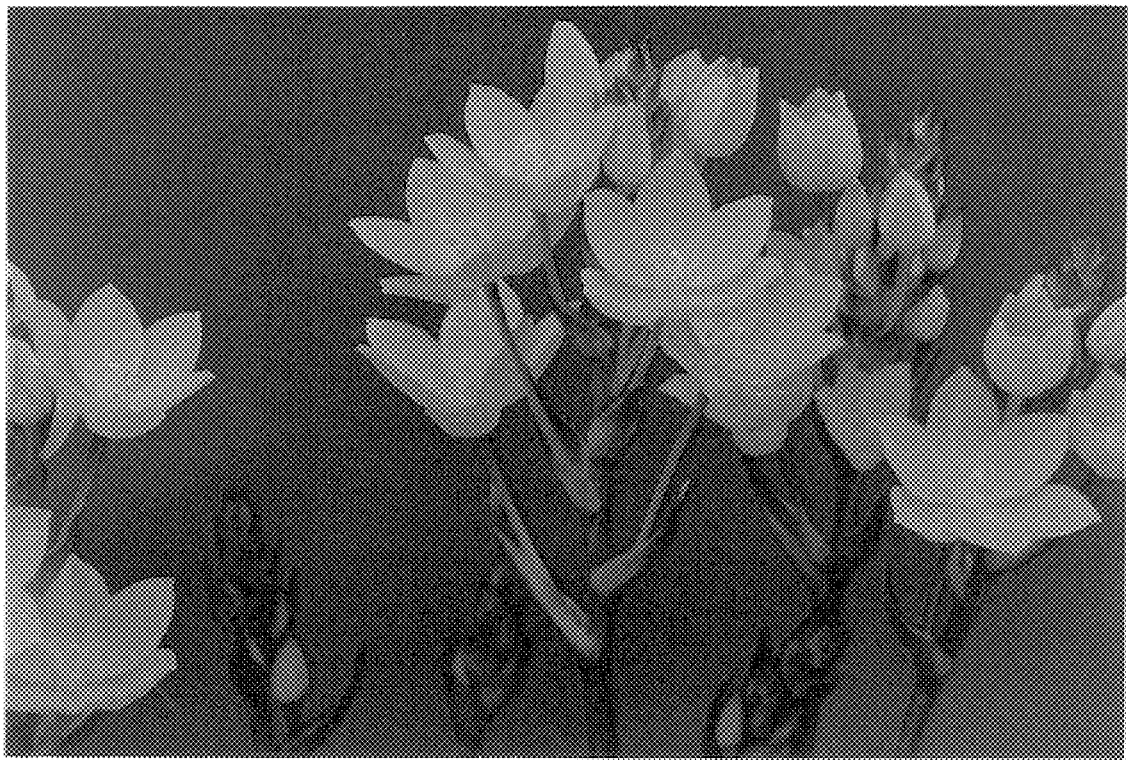
FIG. 2 is a color photograph of the upper portion of a 'Namib Sunrise' plant having a plurality of flowers in full bloom, and several additional flowers beginning to open.

'Namib Sunrise' is an *Ornithogalum dubium* obtained from the open pollination of selected *Ornithogalum dubium* individuals in a greenhouse. Breeding was undertaken in order to obtain a plant suitable for the ornamental potted plant and bulb market.

*Namib Sunrise* was asexually reproduced in Groot Drakenstein, South Africa through tissue culture of leaf explants on a solid "Murishage and Skoop" medium. 'Namib Sunrise' is stable in reproduction because currently approximately 20,000 plants are grown in a soil mixture medium in a tunnel and no instability is observed in the growth of flowering of the propagated material.

At maturity 'Namib Sunrise' consists of a bulb of 2.5 cm to 8 cm in diameter depending on the number of growth cycles and the horticultural conditions. Generally the bulbs are a slightly flattened ovoid sphere, the horizontal diameter being slightly greater than the vertical diameter when the growing point is situated upwards and the roots downwards.

The plant is normally dormant in the summer (December through March at 32 degrees South in the Southern Hemisphere). When dormant substantially all roots and leaves are dried up and no longer visible. In April–May (all descriptions of plants in nature refer to conditions in the South African Province of the Western Cape which is around 30–32 degrees South latitude) growth resumes from the previous year. The exact timing of growth resumption is dependent on seasonal fluctuations in winter rainfall.

Once growth resumes the leaves, roots and bulb expand and grow. Only once substantial bulb, leaf and root growth occur does flower initiation begin. By the time the flower raceme emerges the leaves are perhaps 90% fully grown. The remaining 10% of growth occurs while the flower raceme expands.

Leaves are 8 to 12 cm long when mature, and in shape are linear and strap-like. Generally three to eight leaves are present, and are glabrous. Flowering begins from the lowest flowers on the raceme, and continues upwards with flowers opening over the course of 30 to 60 days. As the flowers open, the raceme itself continues elongating, stretching from an initial height of 15–20 cm to as long as 30 cm upon termination of flowering.

Flower raceme height can be controlled by the level of shade provided. In full sun the raceme height is generally a maximum of 25 cm. As the flowers continue opening up the raceme, the bottom ones senesce. Flowers are not fragrant. Dormancy and senescence of leaves and flowers occur simultaneously upon completion of flowering. As the last flower opens and senesces, the plant begins complete dormancy. For example, bulb growth does not continue after flowering.

In a typical year, flowering begins in October and is complete by December (in the Western Cape). Under the growing conditions in Groot Drakenstein, South Africa, no problems with disease have been experienced while growing 'Namib Sunrise'.

The flowers are shallowly cup-shaped. Flower color is RHS25A orange. The perianth-segments are ovate and 10–20 mm long. The stamens are about half as long, with filaments having fleshy winged membranous involute expansions. The ovary is an oblong ovoid. The ovules are multiseriate. The style is very short. The stigma is capitate, trisulcate, with three decurrent papillate ridges. 15 to 20 flowers are present per inflorescence.

The colors of 'Namib Sunrise' which follow are defined by reference to The Royal Horticultural Society (R.H.S.) Colour Chart. The flower stem is RHS 141C. Upper foliage surface is RHS 141C. Lower foliage surface is RHS 141C. The bulb's scales are white RHS 155D. The bulb is covered with one or two dry scale layers that are cream to light brown (RHS 161C). The seeds are black RHS 202A, approximately 1 mm long and comma-shaped.

The preceding description describes the plant during flowering. Flowering occurs about 4–5 months after planting. Growing condition were as follow: temperature 16–28 degrees C., light level 40% shade as produced by shade cloth over a polyethylene-clad greenhouse corresponding to approximately 2,000 lux, fertilizer was applied as osmicote 14-14-14 at a rate of 5 kg./cubic meter of soil mix, and the plants were irrigated as required. The plants spread to 15 cm after 5 months during flowering in a plastic-covered tunnel.

The flower's ovary develops into the fruit by enlarging if seeds were set. Six tepals are present, shaped as illustrated in FIG. 1. Normally 14–16 flowers open at the same time. An individual bloom will last 7–10 days. The diameter of an individual flower/bloom is 2.8–3.5 cm.

The fruit, a capsule, is oblonged, about 15 mm long. If no seed was set the ovary shrinks and dries together with the petals. The fruit stay on the plant until they release the seed. Seed will only set if pollination was successful by insect or hand pollination. Seed set and fertility is expected to be low.

The leaf has a smooth margin. The tip is lance-shaped. The leaf base is white (RHS 155D) and wide as the leaf.

I claim:

1. A new and distinct cultivar of *Ornithogalum dubium* plant named 'Namib Sunrise', substantially as shown and described.

* * * * *